US012653419B2

(12) United States Patent
Slot et al.

(10) Patent No.: US 12,653,419 B2
(45) Date of Patent: Jun. 16, 2026

(54) SYSTEM WITH A CARDIOLOGICAL SENSOR FOR LUNG FLUID DETECTION

(71) Applicants: UNIWERSYTET LODZKI, Lodz (PL); INSTYTUT CENTRUM ZDROWIA MATKI POLKI, Lodz (PL)

(72) Inventors: Maciej Slot, Lodz (PL); Wielislaw Olejniczak, Lodz (PL); Ilona Zasada, Lodz (PL); Agata Bielecka-Dabrowa, Lodz (PL)

(73) Assignees: UNIWERSYTET LODZKI, Lodz (PL); INSTYTUT CENTRUM ZDROWIA MATKI POLKI, Lodz (PL)

( * ) Notice: Subject to any disclaimer, the term of this patent is extended or adjusted under 35 U.S.C. 154(b) by 0 days.

(21) Appl. No.: 19/118,883

(22) PCT Filed: May 31, 2023

(86) PCT No.: PCT/IB2023/055570
§ 371 (c)(1),
(2) Date: Apr. 7, 2025

(87) PCT Pub. No.: WO2024/074900
PCT Pub. Date: Apr. 11, 2024

(65) Prior Publication Data
US 2026/0007326 A1     Jan. 8, 2026

(30) Foreign Application Priority Data
Oct. 7, 2022     (PL) ........................................ 442466

(51) Int. Cl.
| | |
|---|---|
| A61B 5/0507 | (2021.01) |
| A61B 5/00 | (2006.01) |
| A61B 5/08 | (2006.01) |
| H01Q 1/36 | (2006.01) |
| H01Q 1/52 | (2006.01) |

(52) U.S. Cl.
CPC .............. *A61B 5/08* (2013.01); *A61B 5/0507* (2013.01); *A61B 5/4875* (2013.01); *H01Q 1/362* (2013.01); *H01Q 1/526* (2013.01)

(58) Field of Classification Search
CPC ....... A61B 5/08; A61B 5/0507; A61B 5/4875; H01Q 1/362; H01Q 1/526
See application file for complete search history.

(56) References Cited

U.S. PATENT DOCUMENTS

| | | | |
|---|---|---|---|
| 10,743,815 B2 | 8/2020 | Wyeth et al. | |
| 2010/0249633 A1 | 9/2010 | Droitcour et al. | |
| (Continued) | | | |

FOREIGN PATENT DOCUMENTS

| | | |
|---|---|---|
| EP | 1372477 B1 | 10/2006 |

OTHER PUBLICATIONS

Zelefsky, "Gamma densigraphy in the evaluation of regional pulminary ventilation," Seminars in Nuclear Medicine, vol. 1, Issue 2, Apr. 1971, pp. 216-228.

(Continued)

*Primary Examiner* — Keith M Raymond
*Assistant Examiner* — Milton Truong
(74) *Attorney, Agent, or Firm* — Dinsmore & Shohl LLP

(57) ABSTRACT

The present disclosure relates to a cardiological sensing system for lung fluid detection. The system includes a base to which a movable stand is attached. The stand includes two vertical profiles with a rail connected to the horizontal profile with a rail via angle brackets, and a set of helical antennas oriented parallel to the plane of the base. The set of helical antennas are supported by horizontal crossbars and fixed using the angle brackets with screws to vertical profiles with the rail. Each of the helical antennas includes rectangular shielding made of copper sheet without walls on the side of patient thorax, and an inner cylinder-shaped carcass (Continued)

core with a copper wire wound thereon. A geometric center of the carcass core coincides with a geometric center of a ground and a shield. The helical antennas also include microwave coaxial cables connecting both helical antennas through an N-type coaxial connector with a vector network analyzer through a cable leading to a data analysis computer.

5 Claims, 3 Drawing Sheets

(56) References Cited

U.S. PATENT DOCUMENTS

| | | |
|---|---|---|
| 2012/0179048 A1 | 7/2012 | Mawhinney et al. |
| 2016/0270686 A1 | 9/2016 | Diamond et al. |
| 2017/0135598 A1 | 5/2017 | Weinstein et al. |
| 2018/0049669 A1* | 2/2018 | Vu ........................ A61B 5/0507 |
| 2022/0409082 A1* | 12/2022 | Howie ............... G01R 29/0814 |

OTHER PUBLICATIONS

Sutcliffe et al., "An investigation of an electromagnetic method for the measurement of body composition," Physics in Medicine and Biology, Institute of Physics in Publishing, Sep. 1994, vol. 39, No. 9, pp. 501-507.
Hernigou et al., "Approche diagnostique de l'embolie pulmonaire par l'angioscanner spiraléDiagnostic approach to pulmonary embolism by spiral angioscanner," La Révue de Médecine Interne, vol. 18, Supp. 6, 1997, pp. 613s-619s.

* cited by examiner

SYSTEM WITH A CARDIOLOGICAL SENSOR FOR LUNG FLUID DETECTION

CROSS REFERENCE TO RELATED APPLICATIONS

The present disclosure is a U.S. National Phase of International Patent Application No. PCT/IB2023/055570, entitled "A SYSTEM WITH A CARDIOLOGICAL SENSOR FOR LUNG FLUID DETECTION" and filed May 31, 2023, which claims the priority benefit of Polish Patent Application No. P.442466, filed Oct. 7, 2022, the entire contents of each are incorporated herein.

FIELD

The subject of the present disclosure relates to a cardiological sensor for lung fluid detection.

BACKGROUND

The clinical condition of patients with left ventricular heart failure is characterized by an increased amount of fluid in the lungs, which translates into a change in a physical quantity known as dielectric loss. The direct consequence of this is a decrease in the transmission of electromagnetic waves that can penetrate the patient's rib cage.

SUMMARY

In an aspect, a cardiological sensing system for lung fluid detection includes a base to which a movable stand is attached, the movable stand including two vertical profiles with a rail connected to a horizontal profile via angle brackets. The system further includes a set of helical antennas oriented parallel to a plane of the base. The set of helical antennas are supported by horizontal crossbars and are fixed using the angle brackets with screws to vertical profiles with the rail. Each of the helical antennas include rectangular shielding made of copper sheet without walls on a side of a patient thorax and an inner cylinder-shaped carcass core with a copper wire wound thereon. A geometric center of the inner cylinder-shaped carcass core coincides with a geometric center of a ground and a shield. The system further includes microwave coaxial cables connecting the helical antennas through an N-type coaxial connector with a vector network analyzer through a cable leading to a data analysis computer.

DETAILED DESCRIPTION

Figure 1:
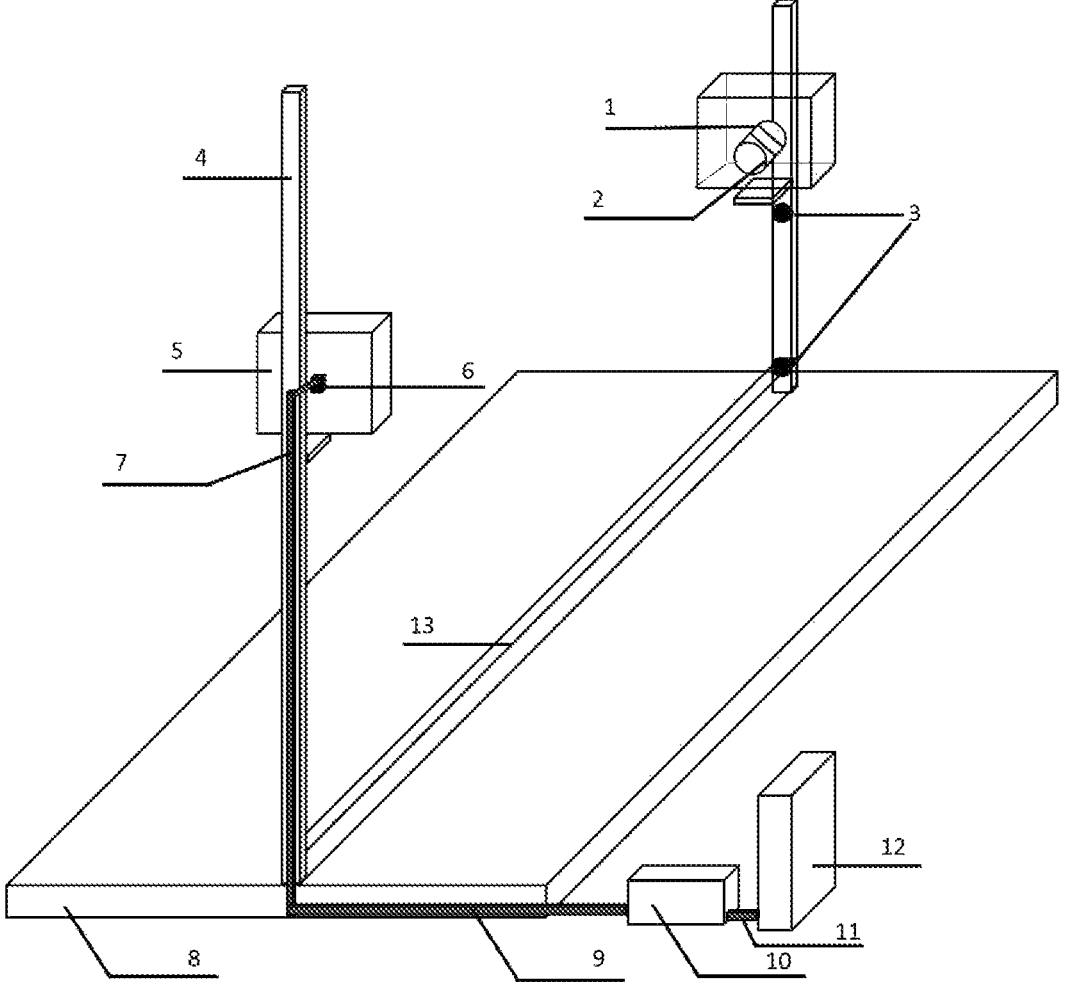
FIG. 1 depicts an isometric projection of a cardiological sensing system according to one or more aspects shown and described herein.

The present disclosure relates to cardiological sensing systems that are used to detect lung fluid in the thorax of a patient. The systems described herein are non-invasive cardiological sensor that are intended for the study of left ventricular heart failure by measuring the amount of transudate in the lungs.

The US application U.S. Pat. No. 4,488,559A discloses a microwave radiometer for passive, non-invasive measurement of fluid content in animal bodies. The radiometer system includes a waveguide antenna that responds to frequencies in the microwave range emitted from the patient's body and is compact in size and light in weight so that it can be easily attached to the patient while resulting in minimal discomfort and loss of mobility. A heating system is attached to the antenna to maintain the temperature of the antenna at a level close to the patient's skin temperature. The associated control circuit processes the signals received from the antenna at one or more frequencies and produces an output signal that correlates with the amount of fluid in the area of the body being examined.

US application US20050107719A1 describes a method for estimating the stroke volume of the heart by taking electrical data from the chest in the first phase of the cardiac cycle, estimating the volume of the heart from a first set of electrical data, then taking a second set of electrical data from the chest in the second phase of the heart cycle, estimating the second heart volume values from the second set of electrical data and using the difference between the first and second heart volume values to estimate cardiac stroke volume.

The U.S. Pat. No. 9,727,986B2 describes a method of creating a 3D visualization of a patient's lung model using an X-ray examination to create a three-dimensional visualization of a patient's lungs based on the images of the patient's lungs taken in computed tomography technology and analyzed by a computer processing unit (CPU).

The application description WO2007105996 describes an implantable medical device and a method for assessing a degree of pulmonary oedema of a patient using an implantable medical device. The method comprises the steps of detecting at least two specific body positions of the patient; then initiating at least one impedance sensing session to sense trans-thoracic impedance signals when the patient is in one position of the at least two specific positions; obtaining impedance values from the impedance signals; determining a relation between respective impedance values at the at least two positions; storing the relation; and using the relation as a metric of pulmonary oedema to assess the degree of pulmonary oedema.

The application US20200297309A1 discloses systems using radio waves to measure the amount of fluid in tissues or the position and cycle of the heart, in combination with electrodes known from electrocardiograms (ECG). The described solution uses the measurement of the dielectric constant change. The measurement is also performed using real-time analyzers, not sweep analyzers.

In the patent description EP3664694A4 one can find a physiological patient monitoring system. It uses a radio signal and a device that measures the amount of fluid in the tissues based on reflection spectroscopy. The device comprises a shielded housing placed over the patch, the patch being configured to be removably attached to or near the patient's skin, the housing containing at least one memory. An antenna located on the housing transmits radio frequency RF waves towards the target portion of the patient's internal tissue and receives the reflected RF waves from the internal tissue. RF circuitry in communication with at least one memory performs an RF-based measurement of the fluid level in the patient's lungs over a period of time.

The publication entitled "UWB pulse propagation into human tissues" (M. Cavagnaro et al. Physics in Medicine & Biology) describes a method for monitoring a person's respiratory status using a radar device located at a distance from the examined person.

The system of the cardiological sensor for lung fluid detection according to the present disclosure includes a wooden base to which a movable stand made of two vertical aluminum profiles with a rail is attached, connected to a horizontal aluminum profile with a rail via angle bars.

The system described herein is equipped with two helical antennas including a cubic shielding (ground and screen) without a wall facing the patient's chest.

The helical antennas are oriented parallel to the plane of the base on the horizontal crossbars supporting them, fastened with screws to the vertical profiles with the rail using angle brackets. Each of the antennas has an inner cylinder-shaped carcass core with a copper wire wound on it, fixed so that its geometric center coincides with the geometric center of the ground and the shield. The system is also equipped with microwave coaxial cables connecting both helical antennas through an N-type coaxial connector with a vector network analyzer connected to the data analysis computer.

The cylindrical carcass core is preferably made of High Impact Polystyrene (HIPS) material.

The screen and the ground are preferably made of copper sheet.

The vertical and the horizontal profiles with the rail are preferably made of aluminum.

The base is preferably made of wood.

The main advantage of the system of the cardiological sensor for lung fluid detection, according to the present disclosure, is the application of a non-invasive system for the study of left ventricular heart failure by using helical antennas shielded from the sides with a significantly reduced height compared to standard helical antennas operating in the axial mode for gigahertz frequencies. The use of low-energy microwave radiation for measurements allows for obtaining results regarding the amount of transudate without the need to use an invasive measurement methods.

An additional advantage of the present disclosure is the adaptation of the dimensions of the antennas to the geometry of the patient while maintaining high directivity and impedance matching for the 50 ohm system.

The design of the system allows for a quick and simple measurements, which in extreme cases can even be performed by the patients themselves as well as provides the opportunity to obtain an immediate result of the examination.

Figure 2:
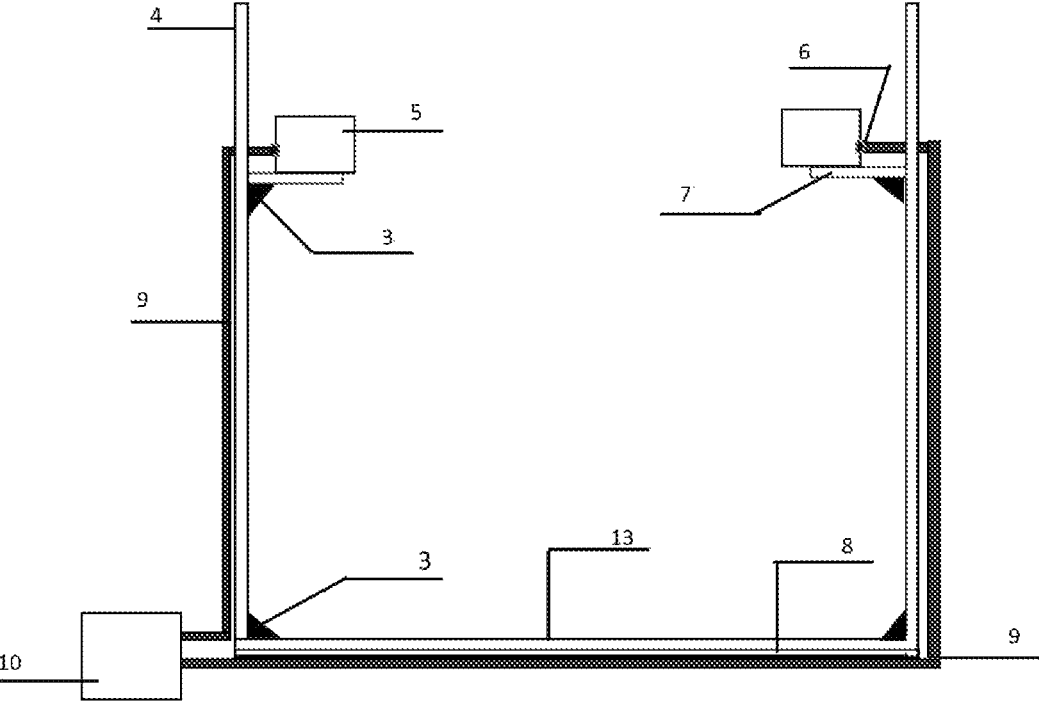
FIG. 2 depicts a cross-sectional view of the system of FIG. 1 according to one or more aspects shown and described herein.
Figure 3:
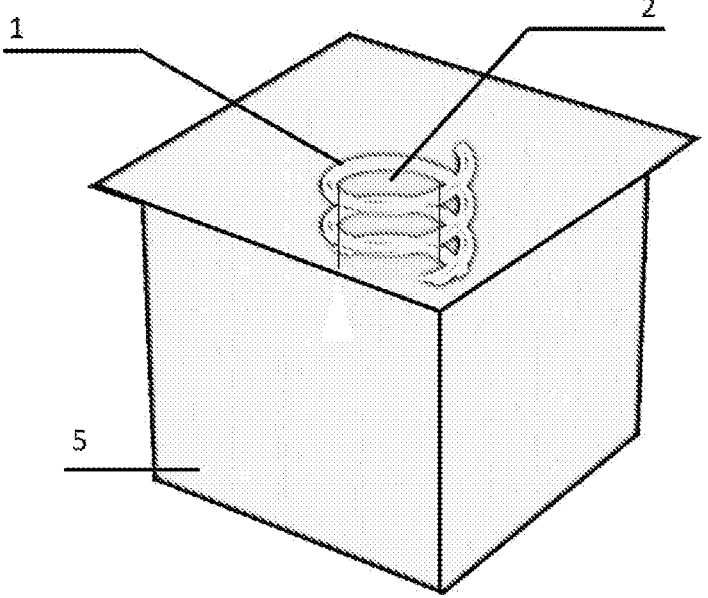
FIG. 3 depicts a schematic view of a helical antenna according to one or more aspects shown and described herein.

The subject of the present disclosure has been shown in an embodiment and in a drawing, in which FIG. 1 shows an isometric projection of the system, FIG. 2 shows a cross-section through the system, and FIG. 3 shows a schematic view of a helical antenna.

The system of the cardiological sensor for lung fluid detection includes wooden base 8, to which a movable stand is attached. The stand includes two vertical aluminum profiles with the rail 4 and the aluminum horizontal profile with the rail 13. The helical antennas 5 are attached to the horizontal aluminum crossbars 7 which are attached to aluminum vertical profiles with the rail 4. The angle brackets 3 are fastened to rails 4 with screws allowing for stiffening or loosening of the clamp. This allows the angle brackets 3 to move freely (in the vertical axis) together with the elements attached to them-horizontal aluminum crossbars 7 on which the helical antennas 5 are placed, so that the transmitting antenna touches the front part of the patient's chest and the receiving antenna touches the patient's back. Each of the helical antennas 5 has the cylinder-shaped inner carcass core 2 (made of HIPS plastic) on which the copper wire 1 is wounded on. The carcass core 2 is fixed so that its geometric center coincides with the geometric center of the cubic shielding made of copper sheet without one wall facing the patient's chest. The helical antennas also include microwave coaxial cables 9 connecting both helical antennas 5 through an N-type coaxial connector 6 with a vector network analyzer 10 through a cable 11 leading to a data analysis computer 12.

The principle of operation of the system consists in performing a measurement, which is carried out by passing a short broadband signal through the patient's rib cage, and then analyzing the attenuation of the signal power by the vector network analyzer 10 and then transferring the data to computer 12 through the cables 11.

The invention claimed is:

1. A cardiological sensing system for lung fluid detection, comprising:
 a base to which a movable stand is attached, the movable stand including two vertical profiles with a rail connected to a horizontal profile via angle brackets; and
 a set of helical antennas oriented parallel to a plane of the base, the set of helical antennas supported by horizontal crossbars and fixed using the angle brackets with screws to vertical profiles with the rail, and each of the helical antennas comprising:
  rectangular shielding made of copper sheet without walls on a side of a patient thorax,
  an inner cylinder-shaped carcass core with a copper wire wound thereon, wherein a geometric center of the inner cylinder-shaped carcass core coincides with a geometric center of a ground and a shield, and
  microwave coaxial cables connecting the helical antennas through an N-type coaxial connector with a vector network analyzer through a cable leading to a data analysis computer.

2. The system according to claim 1, wherein the inner cylinder-shaped carcass core is made of High Impact Polystyrene (HIPS) material.

3. The system according to claim 1, wherein the shield and the ground are made of copper sheet.

4. The system according to claim 1, wherein the vertical profiles with the rail and the horizontal profile with the rail and the horizontal crossbars are made of aluminum.

5. The system according to claim 1, wherein the base is made of wood.

* * * * *